United States Patent [19]
Yoshida et al.

[11] Patent Number: 5,935,827
[45] Date of Patent: Aug. 10, 1999

[54] MALTOSE PHOSPHORYLASE, TREHALOSE PHOSPHORYLASE, NOVEL STRAIN OF GENUS PLESIOMONAS CAPABLE OF PRODUCING THESE ENZYMES AND PROCESS FOR PRODUCING TREHALOSE

[75] Inventors: Masahiro Yoshida; Nobuyuki Nakamura, both of Shizuoka; Koki Horikoshi, Tokyo, all of Japan

[73] Assignee: Nihon Shokuhin Kako Co., Ltd., Tokyo, Japan

[21] Appl. No.: 09/094,583

[22] Filed: Jun. 15, 1998

Related U.S. Application Data

[62] Division of application No. 08/893,504, Jul. 11, 1997, Pat. No. 5,807,719, which is a division of application No. 08/528,923, Sep. 15, 1995, Pat. No. 5,705,378.

[30] Foreign Application Priority Data

| Sep. 16, 1994 | [JP] | Japan | 6-221273 |
| Sep. 16, 1994 | [JP] | Japan | 6-221274 |

[51] Int. Cl.$^6$ .............. C12P 19/12; C12N 9/12; C12N 9/14; C12N 9/24
[52] U.S. Cl. .............. 435/100; 435/194; 435/195; 435/200; 536/123.13
[58] Field of Search ................ 435/194, 200, 435/195, 100; 536/123.13

[56] References Cited

U.S. PATENT DOCUMENTS 5,312,909  5/1994  Driessen et al. .
5,472,863  12/1995 Maruta et al. .................... 435/200

FOREIGN PATENT DOCUMENTS

| 58-216695 | 12/1983 | Japan . |
| 5-292986  | 6/1991  | Japan . |
| 5-91890   | 4/1993  | Japan . |
| 5-184353  | 7/1993  | Japan . |
| 5-211882  | 8/1993  | Japan . |
| 5-292986  | 11/1993 | Japan . |

OTHER PUBLICATIONS

Murao et al, "Enzymatic Synthesis of Trehalose from Maltose", 1985, pp. 2113–2118.

Stewart et al, "The Preparation of Trehalose from Yeast", May 1950, pp. 2059–2061.

"Production of Trehalose by Enzyme Reaction", Abstracts of the Congress of the Agricultural Chemical Society of Japan, 1994.

*Primary Examiner*—Francisco Prats
*Attorney, Agent, or Firm*—Burns, Doane, Swecker & Mathis, L.L.P.

[57] ABSTRACT

Disclosed are a novel microorganism (FERM BP-5144) belonging to the genus Plesiomonas and having ability to produce maltose phosphorylase and trehalose phosphorylase required for the enzymatic production of trehalose and novel maltose phosphorylase and trehalose phosphorylase obtainable from the microorganism as well as a process for producing the enzymes. A novel process for enzymatically producing trehalose (O-α-D-glucopyranosyl-(1→1)-D-glucopyranoside) is also disclosed.

10 Claims, 6 Drawing Sheets

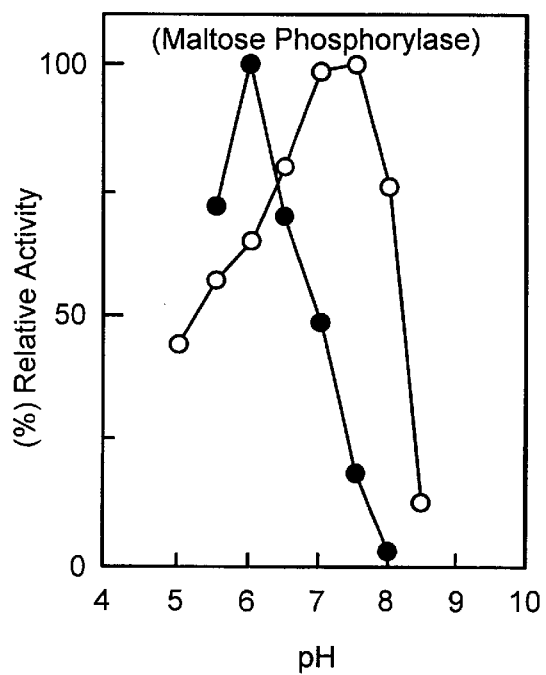 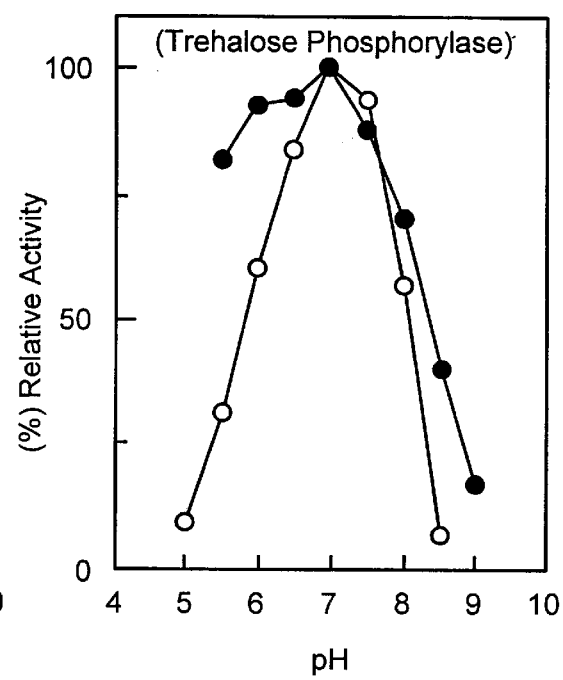

FIG. 3A
FIG. 3B
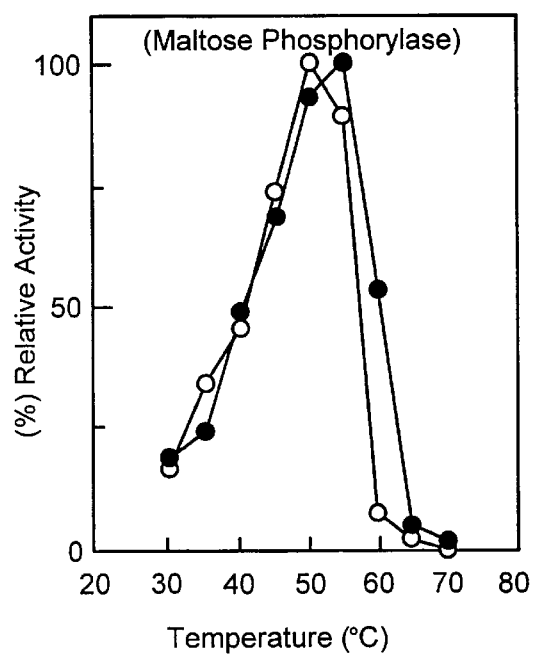
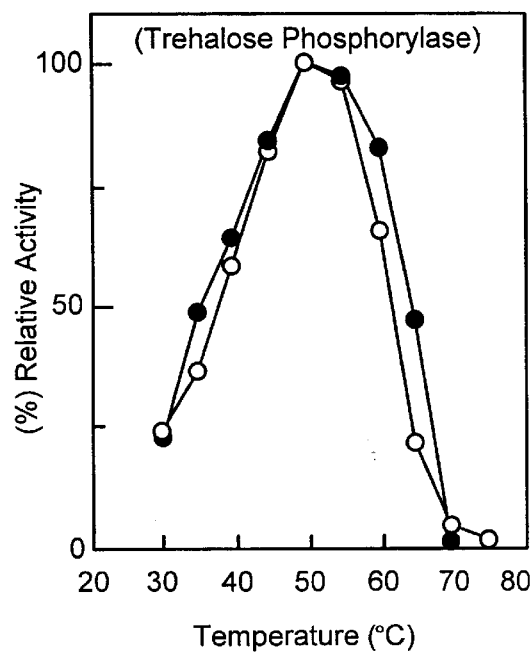

MALTOSE PHOSPHORYLASE, TREHALOSE PHOSPHORYLASE, NOVEL STRAIN OF GENUS PLESIOMONAS CAPABLE OF PRODUCING THESE ENZYMES AND PROCESS FOR PRODUCING TREHALOSE

This application is a divisional of application Ser. No. 08/893,504, filed Jul. 11, 1997, now U.S. Pat. No. 5,807,719, which is a divisional of application Ser. No. 08/528,923, filed Sep. 15, 1995, now U.S. Pat. No. 5,705,378.

BACKGROUND OF THE INVENTION

The present invention relates to a novel microorganism, novel enzymes and a novel process for producing the novel enzymes. More specifically, it relates to a novel microorganism belonging to the genus Plesiomonas and having ability to produce maltose phosphorylase and trehalose phosphorylase required for the enzymatic production of trehalose and novel maltose phosphorylase and trehalose phosphorylase obtainable from the microorganism as well as a process for producing the enzymes.

The present invention further relates to a novel process for enzymatically producing trehalose (O-α-D-glucopyranosyl-(1→1)-D-glucopyranoside).

More precisely, the present invention relates to a process for producing trehalose by utilizing the novel maltose phosphorylase and the novel trehalose phosphorylase derived from the novel microorganism belonging to the genus Plesiomonas.

Trehalose is a material that is expected to be used for various uses such as in pharmaceuticals, cosmetics and foodstuffs. Therefore, various attempts have been made to date to industrially produce trehalose. Those attempts can be roughly classified into three approaches.

One of those is extracting trehalose from microorganisms having ability to accumulate trehalose in their cells (J. Am. Chem. Soc., 72, p2059 (1950); German Patent No. 266584; Japanese Patent Un-examined Publication (KOKAI, hereinafter referred to as "JP-A") 3-130084; JP-A-5-91890; JP-A-5-184353; and JP-A-5-292986). This method comprises steps of culturing microorganisms, isolating the microorganisms, extracting trehalose from the microorganisms, purifying and crystallizing the extracted trehalose, and hence the process steps are very complex. In addition, productivity of trehalose is lower than other processes and a large amount of microbial extraction residue is remained as waste. Therefore, this method cannot be considered an economically efficient process.

For another approach, microorganisms extracellularly secreting trehalose (into their culture media) have been screened and fermentation methods where microorganisms belonging to the genus Brevibacterium, the genus Corynebacterium and the like are cultured to produce trehalose by their extracellular secretion (into their culture media) of trehalose have been developed (JP-A-5-211882). However, also in this approach, production yield, i.e., accumulation amount of trehalose in culture media is not so high (about 3% (W/V)). Therefore, to produce a large amount of trehalose in an industrial scale by this approach, it is necessary to provide a fermentation tank of a large volume and a purification means sufficient for the tank volume and thus this method is not economically advantageous. Further, this method also requires the separation of the microorganisms in order to obtain purified trehalose and, in addition, it requires further complexed steps to eliminate impurities other than trehalose, which have been produced by the microorganisms, and culture medium components.

As a method for solving all of the above-described problems, enzymatic methods have been already developed. As such methods, reported are a process for producing trehalose where maltose phosphorylase derived from microorganisms (Maltose:orthophosphate β-D-glucosyltransferase) and trehalose phosphorylase derived from algaes (α, α-Trehalose:orthophosphate β-D-glucosyltransferase) are allowed to act on maltose in the presence of phosphate (Japanese Patent No. 1513517; Agri. Biol. Chem., 49, p2113 (1985)) and a process for producing trehalose where sucrose phosphorylase derived from bacteria (Sucrose:orthophosphate α-D-glucosyltransferase) and trehalose phosphorylase derived from Basidiomycetes (α, α-Trehalose:orthophosphate α-D-glucosyltransferase) are allowed to act on sucrose in the presence of phosphate (Abstracts of the Congress of the Agricultural Chemical Society of Japan (1994), 3Ra14).

It is reported that trehalose was produced from maltose or sucrose with a high yield of 60 to 70% by these methods. In addition, since the raw materials used in these methods are purified sugars with high purities, trehalose enzymatically produced may be easily purified and hence these methods are considered industrially advantageous as compared with other methods. However, also in this method, the enzymes used for this method, in particular, the trehalose phosphorylase, are derived from algaes or Basidiomycetes such as euglena and grifola, and therefore preparation of the enzymes from these sources is not only economically disadvantageous but also technically difficult. In addition, since optimum pH values of the obtained trehalose phosphorylase, sucrose phosphorylase and maltose phosphorylase used together therewith are quite different from one another, it is very difficult to control a pH value when they are used in combination. Moreover, thermal stability of these enzymes is quite poor and the trehalose production can be carried out only in a low temperature range, for example, 25 to 37° C. and this may lead microbial contamination during the enzymatic reaction when the reaction is carried out in an open reaction tank. Therefore, this method requires strict contamination control to prevent secondary reactions caused by contamination and it may be a drawback of this process. Furthermore, these known enzymes do not permit use of a high concentration of the raw materials when they are used in combination because of their substrate concentration dependency. Therefore, this method also is not an economically efficient method.

With the background described above, it can be said that, if novel maltose phosphorylase and trehalose phosphorylase which are easy to be produced and purified and have high thermal stability and no substrate concentration dependency have been found and become available, it is possible to produce trehalose with high yield and high efficiency from maltose, which is easily available in a large amount.

Therefore, the first object of the present invention is to provide a novel microorganism capable of producing novel enzymes satisfying the various requirements described above, i.e., novel maltose phosphorylase and novel trehalose phosphorylase, with a high production efficiency.

The second object of the present invention is to provide novel maltose phosphorylase and novel trehalose phosphorylase which are easy to be produced and purified and have high thermal stabilities and no substrate concentration dependency.

The third object of the present invention is to provide a process for easily producing the two kinds of enzymes described above with a high yield by utilizing the microorganism mentioned above.

In addition, the forth object of the present invention is to provide a process for producing trehalose by utilizing the novel maltose phosphorylase and the novel trehalose phosphorylase mentioned above and using maltose as a substrate, wherein the enzymatic reactions are possible at a relatively high temperature and at a relatively high substrate concentration and pH value is easily adjusted.

SUMMARY OF THE INVENTION

In order to obtain microorganisms capable of producing maltose phosphorylase and trehalose phosphorylase satisfying the above-described properties required for those enzymes for industrial use, the present inventors had screened various natural sources. As a result, the present inventors had found that a microorganism belonging to the genus Plesiomonas can produce a significant amount of the both enzymes satisfying the requirements described above and thus completed the present invention. Further, the present inventors had found that the objects mentioned above can be achieved by isolating novel maltose phosphorylase and trehalose phosphorylase from the novel microorganism and utilizing the maltose phosphorylase and the trehalose phosphorylase and completed the present invention.

Therefore, the present invention relates to a microorganism (National Institute of Bioscience and Human Technology, FERM BP-5144) having ability to produce maltose phosphorylase and trehalose phosphorylase and belonging to the genus Plesiomonas.

The present invention further relates to maltose phosphorylase having the following physicochemical properties;

(a) Action

The maltose phosphorylase catalyzes cleavage of α-1,4-glucopyranoside bonds in maltose by phosphorolysis in the presence of phosphate to produce glucose and β-D-glucose-1-phosphate and vice versa.

(b) Substrate Specificity (Decomposition Reaction)

It acts on maltose, but not on other disaccharides.

(c) Optimum pH and Stable pH Range

Its optimum pH for the phosphorolytic reaction is 7.0 to 7.5, optimum pH for the synthetic reaction is 6.0; and it is stable within a pH range of 5.5 to 7.0 under heating at 50° C. for 10 minutes.

(d) Thermal Stability

It is stable up to 45° C. under heating at pH 6.0 for 15 minutes.

(e) Optimum Temperature Range for the Action

Its optimum temperature for the phosphorolytic reaction is around 50° C. and its optimum temperature for the synthetic reaction is 50 to 55° C.

(f) Inactivation Conditions

It is completely inactivated at pH 5.0 and 8.0 by heating at 50° C. 10 minutes and also completely inactivated at 55° C. by heating at pH 6.0 for 15 minutes.

(g) Inhibition

It is inhibited by copper, mercury, cadmium, zinc, N-bromosuccinimide, p-chloromercuribenzoate or sodium dodecylbenzenesulfonate.

(h) Isoelectric Point Determined by Isoelectrofocusing

The isoelectric point is pH 3.8 by isoelectrofocusing.

(i) Molecular Weight Measured by SDS Polyacrylamide Gel Electrophoresis

The molecular weight measured by SDS polyacrylamide gel electrophoresis is about 92,000 daltons(molecular weight measured by gel filtration is about 200,000 daltons and hence the enzyme is constituted by two subunits).

The present invention also relates to trehalose phosphorylase having the following physicochemical properties;

(a) Action

The trehalose phosphorylase catalyzes cleavage of α-1,1-glucopyranoside bonds in trehalose by phosphorolysis in the presence of phosphate to produce glucose and β-D-glucose-1-phosphate and vice versa.

(b) Substrate Specificity (Decomposition Reaction)

It acts on trehalose, but not on other disaccharides.

(c) Optimum pH and Stable pH Range

Its optimum pH for the phosphorolytic reaction and the synthetic reaction is 7.0 and it is stable within a pH range of 6.0 to 9.0 under heating at 50° C. for 10 minutes.

(d) Thermal Stability

It is stable up to 50° C. under heating at pH 7.0 for 15 minutes.

(e) Optimum Temperature Range for the Action

Its optimum temperature range for the phosphorolytic and the synthetic reaction is 50 to 55° C.

(f) Inactivation Conditions

It is completely inactivated at pH 5.0 and 9.5 by heating at 50° C. for 10 minutes and also completely inactivated at 55° C. by heating at pH 7.0 for 15 minutes.

(g) Inhibition

It is inhibited by copper, mercury, cadmium, zinc, N-bromosuccinimide, p-chloromercuribenzoate or sodium dodecylbenzenesulfonate.

(h) Isoelectric Point Determined by Isoelectrofocusing

The isoelectric point is pH 4.5 by isoelectrofocusing.

(i) Molecular Weight Measured by SDS Polyacrylamide Gel Electrophoresis

The molecular weight measured by SDS polyacrylamide gel electrophoresis is about 88,000 daltons(molecular weight measured by gel filtration is about 200,000 daltons and hence the enzyme is constituted by two subunits).

In addition, the present invention relates to a process for producing maltose phosphorylase and trehalose phosphorylase comprising culturing the microorganism of the present invention belonging to the genus Plesiomonas, allowing the microorganism to produce and accumulate at least one of the maltose phosphorylase and the trehalose phosphorylase of the invention mentioned above and recovering the enzyme (s).

Further, the present invention relates to a process for producing trehalose comprising allowing the maltose phosphorylase and the trehalose phosphorylase of the present invention to act on maltose in the presence of phosphate.

BRIEF DESCRIPTION OF THE DRAWINGS

FIG. 1 shows optimum reaction pH curves for maltose phosphorylase and trehalose phosphorylase produced by the Plesiomonas strain SH-35 (phosphorolytic reaction (○), synthetic reaction(●)).

FIG. 3 shows optimum reaction temperature curves for maltose phosphorylase and trehalose phosphorylase produced by the Plesiomonas strain SH-35 (phosphorolytic reaction (○), synthetic reaction(●)).

DETAILED DESCRIPTION OF THE INVENTION

Figure 2:
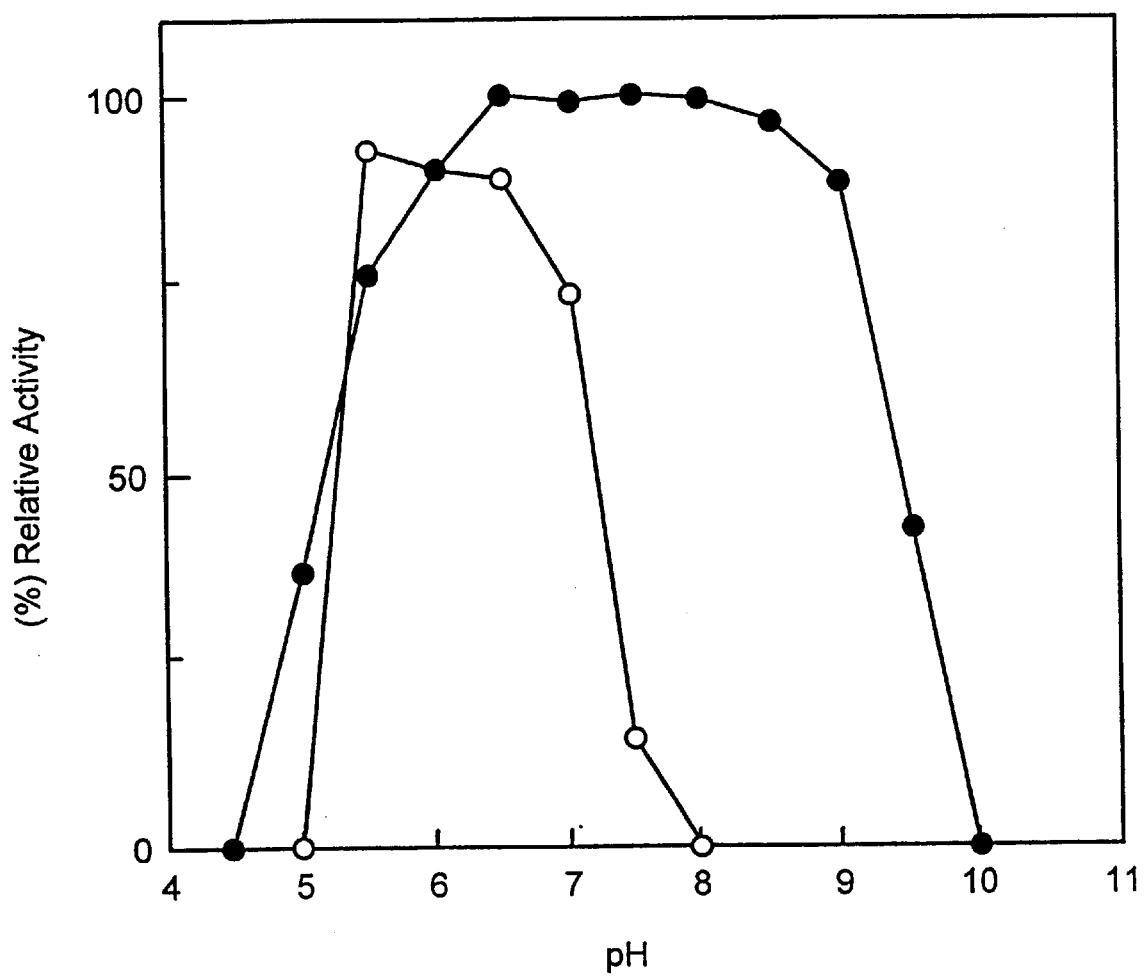
FIG. 2 shows pH stabilities of maltose phosphorylase and trehalose phosphorylase produced by the Plesiomonas strain SH-35 (maltose phosphorylase (○), trehalose phosphorylase (●)).

The present invention will be further explained in detail hereinafter.

The novel strain of the present invention was originally isolated from sludge taken at seashore of Tagonoura, Fuji city, Shizuoka prefecture, Japan. According to the Bergey's Manual of Determinative Bacteriology, 8th Edition, Volume 1, the isolated strain was identified to belong to the genus Plesiomonas and to be an analogous strain of *P. shigelloides* as suggested by the bacteriological properties of the strain shown in Table 1 below.

However, the properties of the strain do not conform to the descriptions of the Bergey's Manual regarding that the strain shows positive results in the VP test and the urease test, that it can metabolize D-mannose, D-galactose, L-arabinose and D-fructose and that it can grow even under alkaline condition of pH 9.0 and, in addition, the strain is quite different from known strains in that it produces and accumulates both of the enzymes, trehalose phosphorylase and maltose phosphorylase, within its cells and in its culture medium (outside of the cells).

The Plesiomonas strain SH-35 was deposited on Jun. 22, 1995 at the National institute of Bioscience and Human Technology 1–3, Higashi 1 chome, Tsukuba-shi, Ibaraki-ken 305, Japan, as FERM BP-5144.

TABLE 1

Bacteriological properties of the maltose phosphorylase and trehalose phosphorylase producing strain 1. Morphology

| | |
|---|---|
| Shape | Rod |
| Size (μm) | (0.6 to 0.7) × 3 |
| Motility | Motile by polar flagella |
| Spore formation | Not formed |

2. Growth in various media

| | |
|---|---|
| Bouillon broth culture | Fairy rings are not formd, whitely opaque |
| Bouillon plate culture | Irregular edge, flat shape, whitely opaque |
| Bouillon slant culture | Spread texitile-like |
| Bouillon gelatin stab culture | Not liquefied gelatin |
| Litmus milk | Not produced asids, not solidified |
| Bouillon broth culture (5% NaCl) | Grown |
| (7% NaCl) | Not grown |

3. Growth pH and temperature

| | |
|---|---|
| Growth pH | 6.0 to 9.0 |
| Growth temperature (°C.) | 15 to 45 |

4. Biochemical properties

| | |
|---|---|
| Reduction of nitrate | − |
| Denitrogenation reaction | + |
| VP test | + |
| MR test | − |
| Indole formation | + − |
| Hydrogen sulfide formation | − |
| Hydrolysis of starch | + |
| Utilization of citric acid | − |
| Liquefaction of gelatin | − |
| Decomposition of casein | − |
| Utilization of inorganic nitrogen | + |
| Pigment formation | − |

TABLE 1-continued

Bacteriological properties of the maltose phosphorylase and trehalose phosphorylase producing strain

| | |
|---|---|
| Urease test | + |
| Catalase test | + |
| Oxidase test | + |
| DNase | − |
| NTPase | − |

4. Biochemical properties

| | |
|---|---|
| OF test | Fermentative |
| Oxygen requirement | Aerobic (grown even under anaerobic condition) |
| GC content | 49.1 mol % |
| 5. Assimilation of sugars | Assimilating D-glucose, D-galactose, D-mannose, L-arabinose, L-sorbose, D-fructose, D-ribose, D-xylose, maltose and trehalose; producing acids and not producing gases from L-arabinose, L-sorbose, D-fructose, D-ribose and D-xylose |

The novel strain of the invention was isolated as follows. First, sludge taken from the seashore was suspended in physiological saline and a drop of the suspension was spread on an agar medium having the composition described below. The used medium contained 2% (w/v) of agar, 1% of trehalose or maltose, 0.5% of polypeptone, 0.5% of yeast extract, 0.1% of dipotassium hydrogenphosphate and 0.02% of magnesium sulfate heptahydrate. The agar plate was incubated at 37° C. under aerobic condition and colonies grown on the plate was recovered and cultured in a broth having the above-described composition except for agar at 37° C. for 24 to 72 hours by shaking at 180 rpm. Then, the culture broth was subjected to centrifugation at 12,000×g at 4° C. for 10 minutes to separate cells from supernatant. The obtained cells were suspended in 0.1 M phosphate buffer (pH 7.0) and activities were determined as described below. As a result, the cells having the taxonomical characteristics described above were separated.

The novel microorganism of the present invention is a bacterium producing novel maltose phosphorylase and trehalose phosphorylase. The process for producing these enzymes will be explained hereinafter.

The microorganism of the present invention (FERM BP-5144) is inoculated into an appropriate medium and cultured. The culture is preferably carried out in a temperature range of from 25 to 42° C. for 8 to 70 hours under aerobic condition. During the cultivation of the microorganism of the present invention, the trehalose phosphorylase and/or the maltose phosphorylase of the present invention are produced. The produced enzymes are chiefly accumulated within the cells and partly accumulated extracellularly (in the medium). Then, the maltose phosphorylase and/or the trehalose phosphorylase produced and accumulated in the cells or outside of the cells (in the medium) are recovered. The culture may be carried out batchwisely or continuously.

The medium used for the cultivation described above will be explained. Trehalose, maltose and sugar materials containing these disaccharides may be used as a carbon source. As a nitrogen source, various organic and inorganic nitrogen compounds can be used and, in addition, the medium may contain various inorganic salts.

When trehalose or a sugar material containing this saccharide is used, the microorganism of the present invention preferentially produce trehalose phosphorylase. When maltose or a sugar material containing this saccharide is used, the microorganism of the present invention produce maltose phosphorylase and trehalose phosphorylase simultaneously. In this case, however, the amount of the produced trehalose phosphorylase tends to be reduced as compared with the case where trehalose is used as a carbon source. Trehalose phosphorylase and maltose phosphorylase can be simultaneously produced by using both of trehalose and maltose or a sugar material containing these saccharides as a carbon source and the producing ratio of trehalose phosphorylase and maltose phosphorylase may be controlled by controlling the amounts of trehalose and maltose.

As the nitrogen source, inexpensive materials or compounds generally used for culturing microorganisms, for example, organic nitrogen sources such as corn steep liquor, soybean meal and various peptones, and inorganic nitrogen sources such as ammonium sulfate, ammonium nitrate, ammonium phosphate and urea. Of course, urea and the organic nitrogen sources may also serve as the carbon source.

Preferred media used for the process of the present invention are, for example, when preferential production of trehalose phosphorylase is desired, broth culture media comprising 1 to 2% (w/v) of trehalose, 2% of yeast extract, 0.15% of ammonium phosphate, 0.15% of urea, 1% of sodium chloride, 0.1% dipotassium hydrogenphosphate, 0.02% of magnesium sulfate heptahydrate and 0.2% of calcium carbonate at a pH of 7.0 to 7.5. When simultaneous production of trehalose phosphorylase and maltose phosphorylase is desired, broth culture media comprising 1 to 2% (w/v) of maltose, 2 to 3% of POLYPEPTON-S (Nippon Seiyaku Co.,Ltd.), 0.15% of ammonium phosphate, 0.15% of urea, 1% of sodium chloride, 0.1% dipotassium hydrogenphosphate, 0.02% of magnesium sulfate heptahydrate and 0.2% of calcium carbonate may be suitably used.

As described above, when maltose is used as the carbon source, not only maltose phosphorylase, but also a certain amount of trehalose phosphorylase is produced. Therefore, to obtain crude enzymes (mixtures of the maltose phosphorylase and the trehalose phosphorylase) for the production of trehalose, it is convenient and economically advantageous to use maltose as the carbon source.

The enzymes accumulated in the cultured cells and in the supernatant of the culture media may be isolated in a conventional manner. The cells containing both enzymes may be also used as an enzyme source for producing trehalose. Further, crude enzymes may be obtained by extracting these enzymes from the cells. The culture supernatant also contains these enzymes and therefore the culture media after removing the cells may also be used as an enzyme source for producing trehalose.

These crude enzymes may be purified by conventional techniques such as solvent precipitation with ethanol, acetone, isopropanol or the like, ammonium sulfate fractionation, ion exchange chromatography and gel filtration chromatography. The maltose phosphorylase and the trehalose phosphorylase can be separated from each other by anion exchange chromatography based on the difference between their isoelectric points.

The enzymes of the present invention obtained as above are, as will be explained in detail in the Examples below, the maltose phosphorylase and the trehalose phosphorylase having the physicochemical properties mentioned above.

Because the Plesiomonas SH-35 strain does not produce α-glucosidase (maltase), glucoamylase, trehalase and the like, which hydrolyze maltose and trehalose, activities of the enzymes can be measured by a simple method where, for the measurement of phosphorolytic activity, the enzymatic reaction is carried out using maltose or trehalose as a substrate in the presence of phosphate and produced glucose is measured by the glucose oxidase method. Activity for the synthetic reaction may be measured by carrying out the reaction with a substrate mixture containing β-D-glucose-1-phosphate and glucose and measuring the amount of inorganic phosphate produced by the enzymatic reaction.

Measurement of Enzyme Activity (1) Phosphorolytic Reaction

To 0.5 ml of 20 mM solution of maltose or trehalose in 50 mM phosphate buffer (pH 7.0), 0.01 ml of the enzyme sample is added to cause the reaction for 15 minutes at 50° C. The enzymatic reaction is stopped by heating in a boiling water bath for 3 minutes. After cooling, the reaction mixture, glucose formed is measured by the glucose oxidase method (GLUCOSE C-II TEST WAKO, Wako Junyaku Kogyo Co.,Ltd.). An amount of the enzyme producing 1 micromole of glucose for 1 minute under the conditions described above is considered one unit of enzyme activity. One unit of the enzyme activity is defined as the amount of enzyme that forms 1 $\mu$mole of glucose per minute under the condition described above.

(2) Synthetic Reaction

To 0.15 ml of 27 mM solution of β-D-glucose-1-phosphate (disodium salt) and glucose of the same concentration in 70 mM HEPES buffer (pH 7.0), 0.05 ml of the enzyme sample is added to cause the reaction for 15 minutes at 50° C. The enzymatic reaction is stopped by heating in a boiling water bath for 2 minutes. Then, inorganic phosphate liberated is measured by P-TEST WAKO (Wako Junyaku Kogyo Co.,Ltd.). One unit of the enzyme activity is defined as the amount of enzyme that forms 1 $\mu$mole of inorganic phosphate per minute under the condition described above.

The novel enzymes of the present invention, the maltose phosphorylase and the trehalose phosphorylase, may be utilized as crude enzymes or purified enzymes. Further, microbial cells having activities of the both enzymes and immobilized cells comprising the microbial cells included in or adsorbed to or chemically bonded to appropriate carriers can be used for, for example, the production of trehalose. Alternatively, the enzymes of the present invention may be used as immobilized enzymes prepared by a known manner.

In the process for the production of trehalose according to the present invention, the two kinds of enzymes mentioned above are allowed to act on maltose in the presence of phosphate. Phosphates are needed for the decomposition of maltose by phosphorolysis and their suitable amount present in the reaction mixture is 0.1 to 500 mmol/liter, preferably 5 to 10 mmol/liter. As the phosphates, inorganic phosphoric acid and salts thereof such as orthophosphoric acid, sodium phosphate, potassium phosphate, sodium dihydrogenphosphate and potassium dihydrogenphosphate may be used. Maltose is used as the substrate. The saccharide containing maltose can also be used as a starting raw material. Maltose is suitably used in a concentration of 10 to 600 g/liter, preferably 200 to 400 g/liter, since such a concentration results in a viscosity easy to be handled and a good yield per batch, i.e., good economical efficiency.

Concentration of the enzymes may be suitably selected considering production yield of trehalose, reaction time and the like. However, suitable concentration is normally 0.1 to 50 units/g (substrate). Reaction temperature may be suitably selected considering the optimum temperatures of the enzymes, reaction time and the like and it is preferably 30 to 65° C., particularly 45 to 55° C. from the viewpoint of prevention of microbial contamination. Reaction pH may be suitably selected from a range of from 5.0 to 9.0, preferably 6.0 to 7.0 considering the optimum pH of the enzymes. Reaction time may also be suitably selected considering production yield of trehalose, amount of the enzymes, volume of reaction vessel and the like. However, suitable reaction time is generally about 50 to 80 hours in industrial production.

The maltose phosphorylase and the trehalose phosphorylase may be used as crude enzymes or purified enzymes. Further, microbial cells having activities of the both enzymes and immobilized cells comprising the microbial cells included in or adsorbed to or chemically bonded to appropriate carriers can be used. Alternatively, the enzymes of the present invention may be used as immobilized enzymes prepared by a known manner. For example, microbial cells immobilized with alginic acid, κ-carrageenin or the like, or extracted enzymes adsorbed on anion exchange resins may be used.

Trehalose produced by the reaction described above can be separated and refined by, like the purification of starch sugars, filtration to remove insoluble materials with diatomaceous earth clay as a filtration aid, deionization with ion exchange resins, chromatographic factionation with ion exchange resins, concentration, crystallization or the like.

EXAMPLES

The present invention will be further explained by referring to the following examples.

EXAMPLE 1
Production and Purification of Intracellular and Extracellular Maltose Phosphorylase The Plesiomonas strain SH-35 (FERM BP-5144) was inoculated into a culture medium containing 1% (w/v) of maltose, 2% of POLYPEPTON-S (Nippon Seiyaku Co., Ltd.), 0.15% of ammonium phosphate, 0.15% of urea, 1% of sodium chloride, 0.1% dipotassium hydrogenphosphate, 0.02% of magnesium sulfate heptahydrate and 0.2% of calcium carbonate (Ph 7.0) and cultured aerobically for 24 hours at 37° C. The obtained culture broth was centrifuged at 12,000×g for 15 minutes at 4° C. to separate it into cells and supernatant. The obtained cells were suspended in a small amount of 20 mM phosphate buffer (pH 7.0) and broken by a ultrasonicator. Then, ammonium sulfate was added to the broken cell suspension to a concentration of 30% saturation and the suspension was left overnight at 4° C. Then, the suspension was centrifuged to remove precipitates and ammonium sulfate was added to the resulting supernatant to a concentration of 70% saturation. The solution was left overnight at 4° C. and produced precipitates were collected and dissolved in 20 mM phosphate buffer (pH 7.0) and then sufficiently dialyzed against the same buffer.

The obtained enzyme was loaded onto a DEAE-Fractogel column (Merck) equilibrated with the same buffer so that the enzyme was adsorbed to the resin. The adsorbed enzyme was eluted with a sodium chloride gradient of from 0 to 0.6 M in the same buffer and concentrated with a UF membrane (YM-30, Amicon). The concentrated enzyme was purified by gel filtration chromatography using a SEPHACRYL S-300 column (Pharmacia) equilibrated with the same buffer containing 0.2 M sodium chloride. Obtained active fractions were combined, dialyzed against the same buffer containing 1.5 M ammonium sulfate and loaded onto a PHENYL TOYOPAL column (Toso) equilibrated with the same buffer containing 1.5 M ammonium sulfate so that the enzyme was adsorbed to the resin. The adsorbed enzyme was eluted with an ammonium sulfate gradient of from 1.5 to 0 M in the same buffer and obtained active fractions were combined and sufficiently dialyzed against the same buffer containing 0.2 M sodium chloride. The enzyme was concentrated with the same UP membrane as that mentioned above and subjected to gel filtration chromatography again using a SUPERDEX 200 column (Pharmacia) equilibrated with the same buffer containing 0.2 M sodium chloride. Obtained active fractions were concentrated as described above (5 ml, about 2,800 units, activity yield; about 28%). The purified intracellular maltose phosphorylase was homogeneous by PAGE and SDS-PAGE.

Using the culture supernatant as a starting material, purified extracellular maltose phosphorylase was also obtained with an activity yield of about 25% (5 ml, about 425 units) through purification and concentration in the same manner as described above.

EXAMPLE 2
Production and Purification of Intracellular and Extracellular Trehalose Phosphorylases The Plesiomonas strain SH-35 (FERM BP-5144) was inoculated into a culture medium containing 1% (w/v) of trehalose, 2% of yeast extract, 0.15% of ammonium phosphate, 0.15% of urea, 1% of sodium chloride, 0.1% of dipotassium hydrogenphosphate, 0.02% of magnesium sulfate heptahydrate and 0.2% of calcium carbonate (pH 7.0). Cultivation and treatments were carried out in the same manner as in Example 1 to give a broken cell suspension and a supernatant. The obtained broken cell suspension and the supernatant were purified by the same manner as in Example 1. Purified intracellular and extracellular trehalose phosphorylases, which were homogeneous exectrophoretically by PAGE and SDS-PAGE, were obtained with activity yields of about 35% (5 ml, about 7,880 units) and about 32% (5 ml, about 2,400 units), respectively.

EXAMPLE 3
Enzymological Properties of the Maltose Phosphorylase and the Trehalose Phosphorylase Produced by the Plesiomonas Strain SH-35

Enzymological properties of the novel maltose phosphorylase and the novel trehalose phosphorylase produced by the Plesiomonas strain SH-35 (FERM BP-5144) were determined by using purified enzymes obtained by the same manner as in Examples 1 and 2 and are shown below. Because intracellular and extracellular trehalose phosphorylases showed similar enzymological properties in preliminary experiments, properties of the intracellular enzyme are shown below.

(a) Action

To a 1% (W/V) solution of maltose and trehalose in 10 mM phosphate buffer (pH 7.0), 5 units (phosphorylitic reaction) per 1 g of each substrate of the maltose phosphorylase or the trehalose phosphorylase was added and allowed to react for 5 hours at 50° C. Then, the enzyme was inactivated by heating in a boiling water bath for 3 minutes. Saccharides except substrates in the reaction digest was identified to glucose and glucose-1-phosphate by the high performance liquid chromatography. Further, 5 units (synthetic reaction) per 1 g of each substrate of the maltose phosphorylase or the trehalose phosphorylase was added to a 1% (W/V) mixed solution of substrates, glucose and β-D-glucose-1-phosphate (disodium salt) or α-D-glucose-1-phosphate (disodium salt), in 10 mM Tris/HCl buffer (pH 7.0) and allowed to react for 5 hours at 50° C. Then, the reaction mixture was treated and sugar composition was determined as described above. As a result, maltose and trehalose were detected in the reaction mixture which had contained glucose and β-D-glucose-1-phosphate, whereas no disaccharide was detected in the reaction mixture which had contained glucose and α-D-glucose-1-phosphate.

The saccharide composition in the reaction mixture was determined as follows. The rection digest obtained after the heat inactivation was passed through a membrane filter (0.45 µm) to remove insoluble materials. Obtained filtrate was used as a sample and analyzed the sugar composition by high performance liquid chromatography using a YMC-Pack ODS-AQ column (AQ-304, YMC) and a mobile phase of water at a column temperature of 30° C. Detection was performed by a differential refractometer.

(b) Substrate Specificity (Phosphorolytic Reaction)

Activities of the both enzymes were determined by using various saccharides instead of the substrates used in the activity measurement (phosphorolytic reaction) described above (maltose and trehalose) and represented as relative activities. Results are shown in Table 2.

TABLE 2

Substrate specificity of the maltose phosphorylase and the trehalose phosphorylase produced by the Plesiomonas strain SH-35

| Substrate | Relative Activity (%) | |
|---|---|---|
| | Maltose phosphorylase | Trehalose phosphorylase |
| Maltose | 100 | 0 |
| Trehalose | 0 | 100 |
| Lactose | 0 | 0 |
| Sucrose | 0 | 0 |
| Melibiose | 0 | 0 |
| Gentiobiose | 0 | 0 |
| Cellobiose | 0 | 0 |
| Isotrehalose | 0 | 0 |
| Kojibiose | 0 | 0 |
| Laminaribiose | 0 | 0 |
| Isomaltose | 0 | 0 |
| Maltotriose | 0 | 0 |
| Maltitol | 0 | 0 |
| Isomaltitol | 0 | 0 |
| Maltothreitol | 0 | 0 |

(c) Optimum pH and Stable pH Range

Optimum pH values for phosphorolytic and synthetic reactions were determined by using the purified enzymes. As a result, it was found that, as shown in FIG. 1A, maltose phosphorylase shows optimum pH in a range of pH 7.0 to 7.5 for the phosphorolitic reaction (○), and at 6.0 for the synthetic reaction (●). Further, as shown in FIG. 1B, it was found that optimum pH of the trehalose phosphorylase was pH 7.0 for both of the phosphorolytic reaction (○) and the synthetic reaction (●). The pH value was adjusted by using 20 mM phosphate buffer in the phosphorolytic reaction, and by using MES (pH 5.5 to 6.5), MOPS (pH 6.5 to 7.0), HEPES (pH 7.0 to 8.0) and Tris/HCl (pH 7.5 to 9.0) buffers in the synthetic reaction.

Further, after treating both of the enzymes in each of the buffers for 10 minutes at 50° C., remaining activities of the enzymes were determined with respect to the phosphorolytic reaction. As a resulc, as shown in FIG. 2, it was found that maltose phosphorylase (○) is stable in a pH range of 5.5 to 6.5, and trehalose phosphorylase (●) is stable in a pH range of 6.0 to 9.0. In this case, the pH value was adjusted by using acetate (pH 5.0 to 5.5), phosphate (pH 6.0 to 8.0) and carbonate (pH 8.9) buffers.

(d) Optimum Temperature for the Action

Optimum temperatures of the both enzymes were determined for the phosphorolytic reaction and the synthetic reaction. As a result, as shown in FIG. 3, both of the maltose phosphorylase (A, ○; phosphorolytic reaction, ●; synthetic reaction) and the trehalose phosphorylase (B, ○; phosphorolytic reaction, ●; synthetic reaction) showed optimum temperatures of 50° C. for the phosphorolytic reaction and 50 to 55° C. for the synthetic reaction.

(e) Thermal Stability

Figure 4:
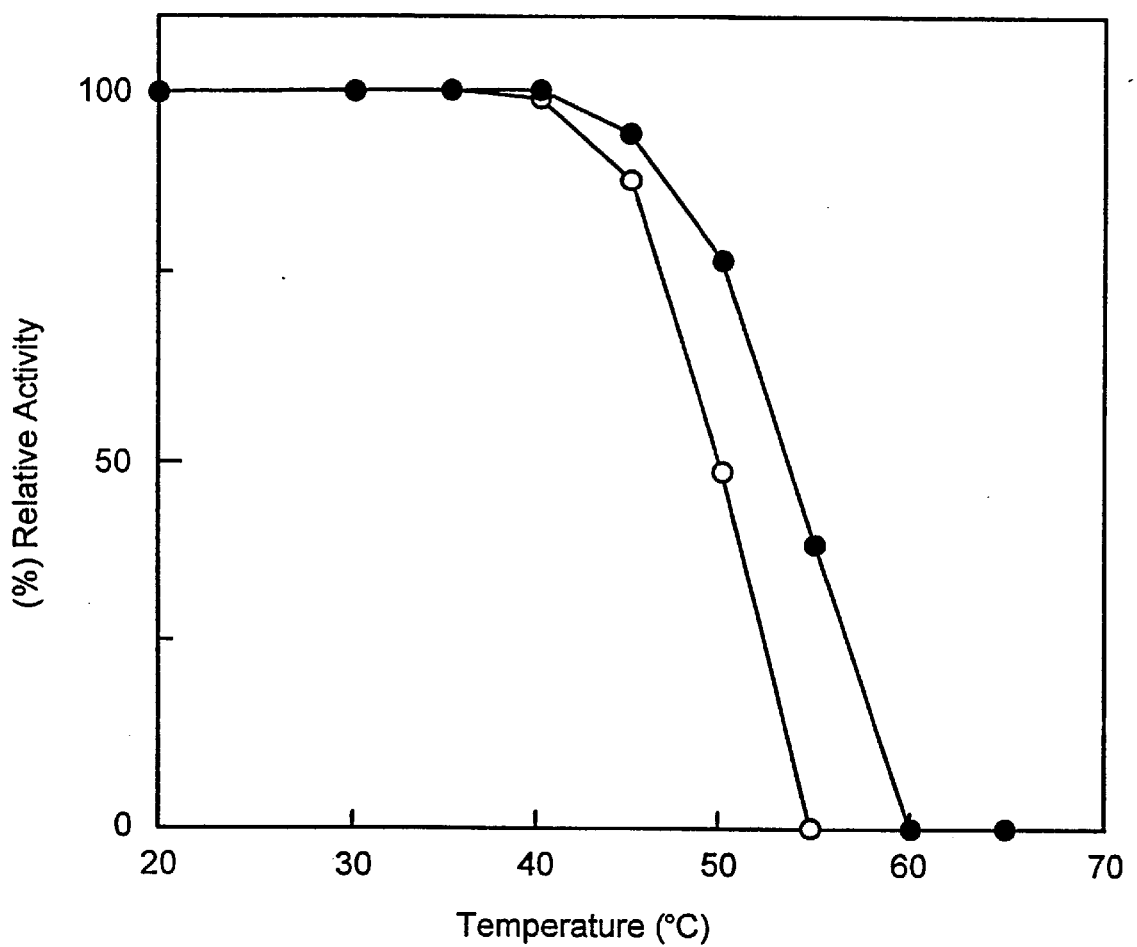
FIG. 4 shows thermal stabilities of maltose phosphorylase and trehalose phosphorylase produced by the Plesiomonas strain SH-35 (maltose phosphorylase (○), trehalose phosphorylase (●)).

After treating the maltose phosphorylase and the trehalose phosphorylase at their stable pH values (pH 6.0 and 7.0, respectively) and various temperatures for 15 minutes, remaining activities of the both enzymes were determined in a conventional manner by comparing with those of untreated enzymes which were stored in an ice bath. As a result, as shown in FIG. 4, the maltose phosphorylase (○) was completely inactivated at 55° C. and the trehalose phosphorylase (●) was completely inactivated at 60° C.

(f) Inhibitor

Activities of the both enzymes were determined in the presence of various metalic salts and chemicals, and results are shown in Table 3 as relative activities based on the activities in the absence or inhibitor which are considered as 100%.

TABLE 3

Effects of various metalic salts and chemicals on the phosphorolytic activities or maltose phosphorylase and trehalose phosphorylase produced by the Plesiomonas strain SH-35

Figure 5:
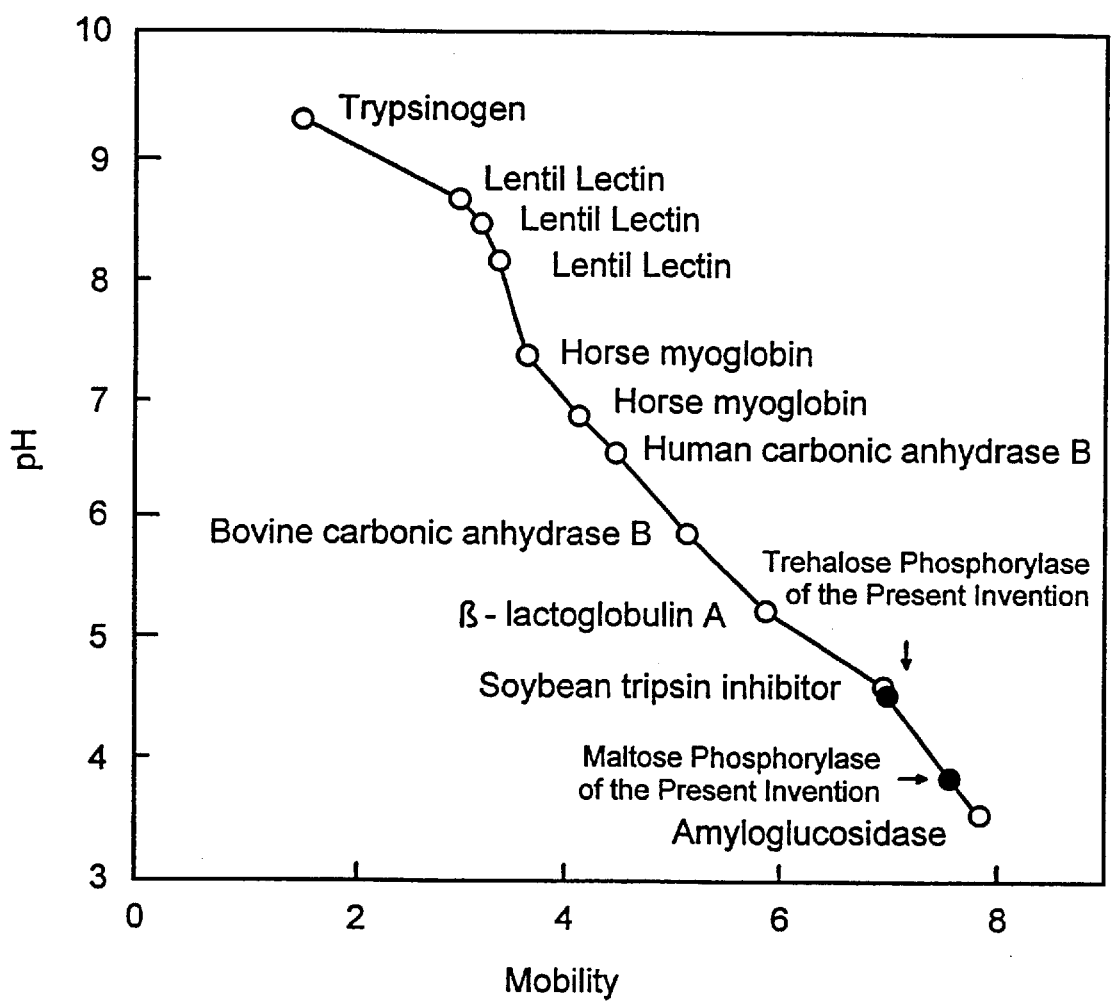
FIG. 5 shows isoelectric points of maltose phosphorylase and trehalose phosphorylase produced by the Plesiomonas strain SH-35.

| Inhibitor | mM | Relative Activity (%) | |
|---|---|---|---|
| | | Maltose phosphorylase | Trehalose phosphorylase |
| Not added | 0 | 100 | 100 |
| LiCl | 1 | 98 | 97 |
| KCl | 1 | 99 | 97 |
| NaCl | 1 | 100 | 93 |
| BaCl$_2$ | 1 | 100 | 99 |
| CaCl$_2$ | 1 | 103 | 102 |
| CdCl$_2$ | 1 | 10 | 30 |
| CoCl$_2$ | 1 | 61 | 61 |
| CuCl$_2$ | 1 | 5 | 9 |
| HgCl$_2$ | 1 | 0 | 0 |
| MgCl$_2$ | 1 | 89 | 82 |
| MnCl$_2$ | 1 | 106 | 94 |
| NiCl$_2$ | 1 | 81 | 56 |
| FeCl$_3$ | 1 | 107 | 94 |
| PbCl$_2$ | 1 | 113 | 98 |
| SnCl$_2$ | 1 | 110 | 97 |
| ZnCl$_2$ | 1 | 16 | 13 |
| FeCl$_3$ | 1 | 86 | 79 |
| EDTA | 1 | 108 | 101 |
| IAA | 1 | 101 | 89 |
| NBS | 1 | 11 | 9 |
| pCMB | 1 | 11 | 8 |
| PMSF | 1 | 67 | 74 |
| SDS | 1% | 0 | 61 | mM; Concentration
EDTA; Ethylenediaminetetraacetate, IAA; Monoiodoacetate,
NBS; N-Bromosuccinimide, pCMB; p-Chloromercuribenzoate,
pMSF; p-Methylsulfonyl fluoride,
SDS; Sodium dodecylbenzenesulfonate (g) Isoelectric Point Isoelectric points of the both enzymes were determined by isoelectrofocusing using ISOGEL (MFC BioProducto). As a result, the maltose phosphorylase has an isoelectric point of 3.8 and the trehalose phosphorylase has that of 4.5 as shown in FIG. 5.

(h) Molecular Weight

Figure 6A:
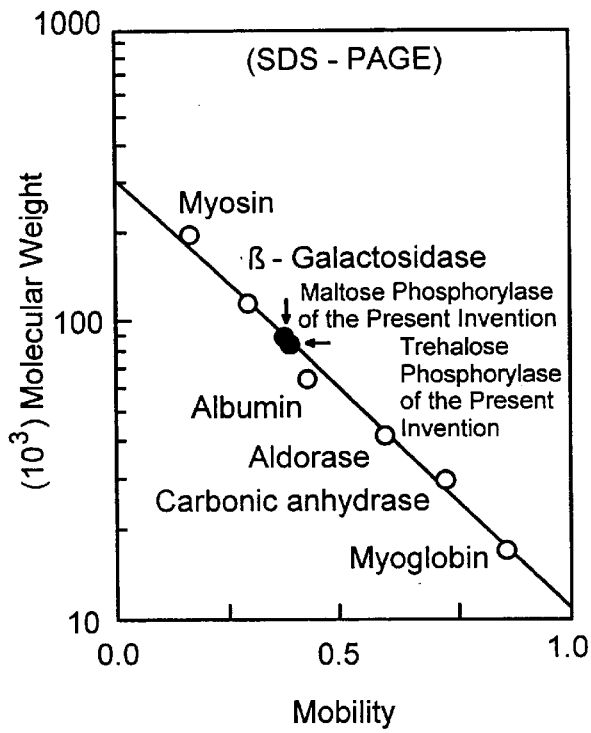
FIG. 6 shows molecular weights of maltose phosphorylase and trehalose phosphorylase produced by the Plesiomonas strain SH-35.
Figure 6B:
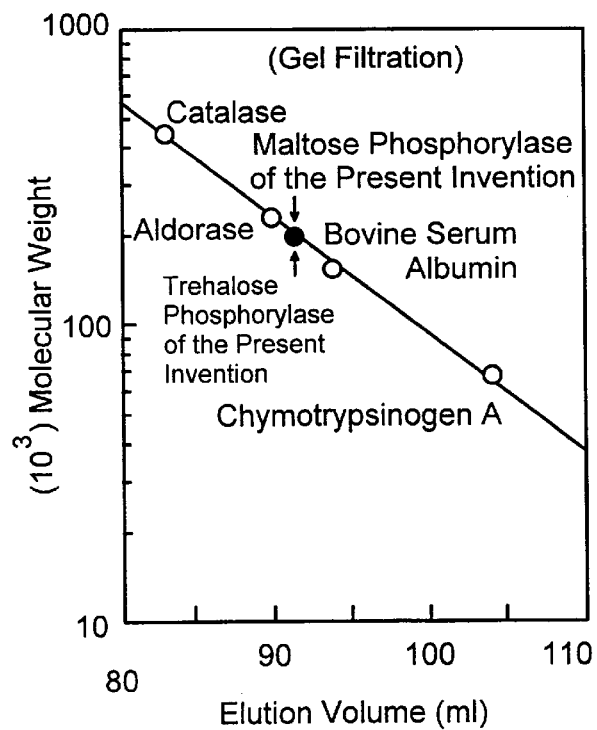

Molecular weights of the both enzymes were determined by SDS-PAGE and gel filtration using SEPHACRYL S-200. As a result, as shown in FIG. 6, molecular weights of the both enzymes were determined as about 200,000 daltons by gel filtration, whereas SDS-PAGE showed that the maltose phosphorylase has a molecular weight of about 92,000 daltons and the trehalose phosphorylase has that of 88,000 daltons. Therefore, it is expected that each of these enzymes is constituted by two subunits.

The physicochemical properties mentioned above are shown in Tables 4 and 5 together with those of known maltose phosphorylases and trehalose phosphorylases.

TABLE 4

Physicochemical Properties of Maltose Phosphorylases of Various Origins

|  | Maltose phsphorylase of the present invention | Agric. Biol. Chem. 37, p2813 (1973) | JP-A-1-91778 |
|---|---|---|---|
| Microorganism | Plesiomonas strain SH-35 (bacterium) | *Lactobacillus brevis* (bacterium) | *Lactobacillus sanfransisco* (bacterium) |
| Location of enzyme | Present within cells and in culture supernatant | Present within cells | Present within cells |
| Optimum pH |  |  |  |
| Decomposition reaction | 7.0–7.5 | 5.4 | 5.5 |
| Synthesis reaction | 6.0 | Not described | Not described |
| Optimum temperature |  |  |  |
| Decomposition reaction | 50° C. | 50° C. | 40–50° C. |
| Synthesis reaction | 50–55° C. | Not described | Not described |
| Thermal stability | After treatment at pH 6.0 for 15 minutes, stable up to 45° C., and completely deactivated at 55° C. | After treatment at pH 5.4 for 30 minutes, stable up to 35° C., and completely deactivated at 50° C. | After treatment for 15 minutes, stable up to 40° C., and completely deactivated at 60° C. |
| Isoelectric point | 3.8 | Not described | Not described |
| Molecular weight |  |  |  |
| SDS-PAGE | about 92,000 | about 80,000 | Not described |
| Gel filtration | about 200,000 | about 150,000 | about 150,000 |
| Glucose-1-phosphate product | β | β | β |
| Substrate specificity (decomposition reaction) | Acting on maltose, not acting on the other disaccharides | Acting on maltose, not acting on isomaltose and maltotriose | Acting on maltose, not acting on the other disaccharides |

TABLE 5

Physicochemical Properties of Trehalose Phosphorylases of Various Origins

|  | Trehalose phsphorylase of the present invention | Agric. Biol. Chem., 49, p2113 (1985) | Abs. of Cong. of Agric. Chem. Soc. Jpn. (1994) 3Ra14 | FEMS Microbiol. Lett., 55, p147 (1988) |
|---|---|---|---|---|
| Microorganism | Plesiomonas strain SH-35 (bacterium) | *Euglena gracilis* (green algae) | *Grifola frondosa* (Basidiomycetes) | *Flammulina velutipes* (Basidiomycetes) |
| Location of enzyme | Present within cells and in culture supernatant | Present within cells | Present within basidiocarps | Present within conidiospores and basidiocarps |
| Optimum pH |  |  |  |  |
| Decomposition reaction | 7.0 | 7.0 | 6.0–7.0 | 7.0 |
| Synthesis reaction | 7.0 | 6.0 | Not described | 6.3 |
| Optimum temperature |  |  |  |  |
| Decomposition reaction | 50° C. | 40° C. | 35–37° C. | 30° C. |
| Synthesis reaction | 50–55° C. | Not described |  |  |
| Thermal stability | After treatment at pH 7.0 for 15 minutes, stable up to 48° C., and completely deactivated at 60° C. | After treatment at pH 7.0 for 30 minutes, stable up to 40° C. | After treatment for 30 minutes, stable up to | Not described 35° C. |
| Molecular weight |  |  |  |  |
| SDS-PAGE | about 88,000 | Not described | about 60,000 | Not described |
| Gel filtration | about 200,000 | 344,000 | about 120,000 |  |
| Isoelectric point | 4.5 | Not described | Not described | Not described |
| Glucose-1-phosphate product | β | β | α | α |
| Substrate specificity (decomposition reaction) | Acting on trehalose, not acting on the other disaccharides | Acting on trehalose | Acting on trehalose | Acting on trehalose |

EXAMPLE 4
Production of Intracellular and Extracellular Trehalose Phosphorylases To 20 liters of a culture medium containing 1% (w/v) of trehalose, 2% of yeast extract (Difco), 0.15% of ammonium phosphate, 0.15% of urea, 1% of sodium chloride, 0.1% dipotassium hydrogenphosphate, 0.02% of magnesium sulfate heptahydrate and 0.2% of calcium carbonate (pH 7.5), 1 liter of the seed culture of Plesiomonas strain SE-35 (FERM BP-5144) obtained by preliminarily cultured the strain in the same medium overnight was added under sterile condition and cultured under aerobic conditions of 300 rpm of agitation and an aeration rate of 1 v.v.m for 24 hours at 37° C. The obtained culture broth was assayed for trehalose phosphorylase activity and it was found to have the activity of 1.5 units per ml. Maltose phosphorylase activity was also assayed, but it was feeble activity.

Then, the culture broth was centrifuged at 12,000×g for 10 minutes at 4° C. to obtain about 160 g of cells (wet weight) and 19.5 liters of the supernatant. The supernatant was concentrated with a UF membrane (YM-30, Romicon) to give about one liter (about 6,400 units) of the concentrated extracellular enzyme. The trehalose phosphorylase activity in the supernatant was measured and found to be about 25% (about $7.5 \times 10^3$ units) of the total activity (about $30 \times 10^3$ units).

The cells were sufficiently washed with 10 mM phosphate buffer (pH 7.0), suspended in 500 ml of the same buffer and broken by a ultrasonicator. The phosphorolytic activity of trehalase phosphorylase was measured by the same manner as described above and it was found that about 75% ($22.5 \times 10^3$ units) of the total activity was contained in the cells.

EXAMPLE 5
Production of Intracellular and Extracellular Enzymes Containing the Maltose Phosphorylase and the Trehalose Phosphorylase The strain SH-35 (FERM BP-5144) was cultured in the same manner as in Example 1 except that, among the culture medium components, trehalose and yeast extract were replaced with maltose and 5% of POLYPEPTON-FC (Nippon Seiyaku Co.,Ltd), respectively. Maltose phosphorylase activity and trehalose phosphorylase activity in the culture broth were measured and it was found that the broth had 0.5 units of maltose phosphorylase activity and 0.45 units of trehalose phosphorylase activity per ml, respectively. Then, the culture medium was centrifuged similarly to give about 150 g of cells (wet weight) and 19.6 liters of the supernatant. Maltose phosphorylase activity in the cells and the supernatant was measured and it was found that, based on the total activity, the cells contained about 78% of the activity (about 10,000 units) and about 22% of the activity was contained in the outside of the cells (in the culture supernatant). Further, about 82% of the trehalose phosphorylase activity (about 9,000 units) based on the total activity was contained in the cells and about 18% of the activity was contained in the outside of the cells (in the culture supernatant). The culture supernatant was concentrated in a manner similar to that of Example 1 to give about 1 liter of concentrated enzymes, and the concentrated enzymes contained about 1,700 units of the maltose phosphorylase and 1,430 units of the trehalose phosphorylase.

EXAMPLE 6

Purified intracellular trehalose phosphorylase and purified intracellular maltose phosphorylase produced in the same manners as in Examples 2 and 1 were added to 10 ml of 10, 20, 30 and 40% (W/V) solutions of maltose in 10 mM phosphate buffer (pH 6.0) in an amount of 5 units (phosphorolytic activity) per 1 g of the substrate and allowed to react for 70 hours at 55° C. After the reaction was completed, the enzymes were inactivated by heating the reaction mixtures at 100° C. for 5 minutes and trehalose contents in the resulting saccharified mixtures were determined. As a result, it was found that 58.2, 58.1, 58.6 and 57.9% of trehalose based on the weight of the substrate was produced.

In the above, the quantitative determination of trehalose was performed as follows.

After diluting a saccharified reaction mixture, which was inactivated by heating, with water to 1% (W/V), 0.01 units of glucoamylase (pure grade 30 U/mg, Seikagaku Kogyo Co.,Ltd) was added to 0.5 ml of the mixture and allowed to react at pH 5.0 for 1 hour at 50° C. to completely decompose unreacted maltose into glucose. Then, the reaction mixture was heated in boiling water bath at 100° C. for 5 minutes to inactivate glucoamylase. After removing insoluble materials with a UF membrane filter (0.45 μm), the trehalose content of the resulting filtrate was measured by the HPLC method using a YMC-Pack ODS-AQ column (AQ-304, YMC) and water as a mobile phase at a column temperature of 30° C. Detection was performed by differential refractometer.

EXAMPLE 7

Five units each per 1 g of the substrates of purified extracellular trehalose phosphorylase and purified extracellular maltose phosphorylase produced in the same manners as in Examples 2 and 1 were added to 10 ml of 20% (W/V) solution of high maltose syrup (trade name; MC-95, Nihon Shokuhin Kako Co.,Ltd, Sugar composition; 2.5% of glucose, 95.2% of maltose, 0.8% of maltotriose and 1.5% of maltotetraose) containing 5 mM phosphate buffer (pH 6.0) and allowed to react as in Example 6. Trehalose formed was measured by the HPLC method described above and it was found to correspond to 54.3% of the weight of the used substrates.

EXAMPLE 8

In the same manner as in Example 7, 1 kg of the cells (wet weight) containing the trehalose phosphorylase and the maltose phosphorylase were obtained. Phosphorolytic enzyme activities of the both enzymes were measured in a conventional manner and it was found that the cells had 55 units/g (wet weight) of trehalose phosphorylase activity and 68 units/g (wet weight) of maltose phosphorylase activity. To 250 liters of a 30% (w/v) maltose solution in 10 mM phosphate buffer (pH 6.5), 1 kg of the produced cells were added and allowed to react for 80 hours at 50° C. After removing the cells by centrifugation, a portion of resulting supernatant was treated with glucoamylase and its sugar composition was assayed by HPLC. As a result, it was found that the composition was 58.1% of trehalose, 39.6% of glucose and 2.3% of glucose-1-phosphate.

To 240 liters of the obtained saccharified supernatant (solid content; 72 kg), 0.1% of crude glucoamylase (trade name; SUMIZYME #3000, Shin-Nippon Kagaku Co.,Ltd.) based on the solid content was added and allowed saccharification again at pH 5.5 for 20 hours at 55° C. to hydrolyze substantially all of remaining maltose into glucose. Then, it was purified by conventional techniques including decoloration by activated charcoal and deionization with ion exchange resins and concentration under reduced pressure to give a purified saccharified mixture (solid content; about 65 kg) of a concentration of about 75% (W/V).

According to the present invention, a novel microorganism capable of producing maltose phosphorylase and trehalose phosphorylase, which are required for the enzymatic production of trehalose, intracellularly and extracellularly is provided. Since the microorganism of the present invention is a bacterium, the enzymes may be obtained from its cells more easily than from green algaes, Basidiomycetes and the like which have been known as sources of trehalose phosphorylase and, in addition, culture period may be markedly shortened and therefore the microorganism is economically advantageous. Further, the microorganism of the present invention is also advantageous with respect to the fact that the one kind of the bacterium can simultaneously produce two kinds of the enzymes required for the enzymatic production of trehalose.

Further, since the both enzymes of the present invention satisfy the properties required for the enzymatic production of trehalose, they make it very easy to effectively utilize produced trehalose and ensure remarkable improvement of economical efficiency. For example, since the maltose phosphorylase and the trehalose phosphorylase of the present invention show high thermal stability and hence they are capable of catalyzing the reactions at a high temperature, microbial contamination during the reactions may be effectively avoided. In addition, since the both enzymes have similar optimum pH ranges for their actions, they can advantageously eliminate the need of troublesome pH control during the reaction.

Moreover, according to the present invention, trehalose can be enzymatically produced by using the novel maltose phosphorylase and the trehalose phosphorylase.

Furthermore, in the process for producing trehalose according to the present invention, pH control is very easy and it is possible to obtain a high trehalose yield even with a high substrate (maltose) concentration. Further, it is possible to use a high reaction temperature and, by selecting a high reaction temperature, trehalose can be obtained with a high yield. Further, since the enzymatic reaction is possible at a high temperature, microbial contamination can be eliminated during the reaction.

What is claimed is:

1. Purified maltose phosphorylase having the following physicochemical properties:

(a) Action:
   Cleaving α-1,4-glucopyranosidic bonds in maltose by phosphorolysis in the presence of phosphate to produce glucose and β-D-glucose-1-phosphate and vice versa;

(b) Substrate specificity (phosphorolytic reaction):
   Acting on maltose, not on other disaccharides, (c) Optimum pH and stable pH range:
   Optimum pH for phosphorolytic reaction of 7.0 to 7.5 and optimum pH for synthetic reaction of 6.0; and stable within a pH range of 5.5 to 7.0 under heating at 50° C. for 10 minutes, (d) Thermal stability:
   Stable up to 45° C. under heating at pH 6.0 for 15 minutes, (e) Optimum temperature range for the action:
   Optimum temperature for phosphorolytic reaction of around 50° C. and optimum temperature for synthetic reaction of 50 to 55° C., (f) Inactivation:
   Completely inactivated at pH 5.0 and 8.0 by heating at 50° C. for 10 minutes and also completely inactivated at 55° C. by heating at pH 6.0 for 15 minutes, (g) Inhibition:
   Inhibited by copper, mercury, cadmium, zinc, N-bromosuccinimide, p-chloromercuribenzoate or sodium dodecylbenzenesulfonate, (h) Isoelectric point determined by isoelectrofocusing:
   3.8, and (i) Molecular weight measured by SDS-polyacrylamide gel electrophoresis:
   about 92,000 daltons (molecular weight measured by gel filtration is about 200,000 daltons and the enzyme is constituted by two subunits).

2. A process for the production of trehalose wherein the maltose phosphorylase of claim 1 and a trehalose phosphorylase are allowed to act on maltose in the presence of phosphate.

3. A process of claim 2 wherein enzymatic reactions are carried out in a temperature range of from 30 to 65° C.

4. The process of claim 2, wherein the maltose is used in the form of a maltose containing aqueous solution and the resulting aqueous solution containing trehalose and maltose is concentrated to produce a saccharide solution containing trehalose.

5. The process of claim 4, wherein the maltose containing aqueous solution is an aqueous solution containing maltose or an aqueous solution containing maltose and other saccharides.

6. The process of claim 4, wherein the aqueous solution containing trehalose and maltose is concentrated to the extent that any saccharides are not crystallized.

7. The process of claim 4, wherein the aqueous solution containing trehalose and maltose contains saccharides other than trehalose and maltose.

8. The process of claim 2, wherein the maltose is used in the form of a maltose containing aqueous solution; the resulting aqueous solution containing trehalose and maltose is reacted with glucoamylase; and the resulting aqueous solution containing trehalose and glucose or aqueous solution containing trehalose, glucose and maltose is concentrated to produce a saccharide solution containing trehalose.

9. The process of claim 8, wherein the aqueous solution containing trehalose and maltose or aqueous solution containing trehalose, glucose and maltose is concentrated to the extent that any saccharides are not crystallized.

10. The process of claim 8, wherein the aqueous solution containing trehalose and maltose or aqueous solution containing trehalose, glucose and maltose or aqueous solution containing trehalose, glucose and maltose contains saccharides other than trehalose, glucose and maltose.

* * * * *